US009532758B2

(12) United States Patent
Zaiki

(10) Patent No.: US 9,532,758 B2
(45) Date of Patent: Jan. 3, 2017

(54) X-RAY DIAGNOSTIC APPARATUS AND INJECTOR

(71) Applicant: Toshiba Medical Systems Corporation, Otawara-shi (JP)

(72) Inventor: Ryuji Zaiki, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/721,292

(22) Filed: May 26, 2015

(65) Prior Publication Data

US 2015/0250437 A1   Sep. 10, 2015

Related U.S. Application Data

(63) Continuation-in-part of application No. PCT/JP2013/081976, filed on Nov. 27, 2013.

(30) Foreign Application Priority Data

Nov. 27, 2012   (JP) ................................ 2012-259022
Nov. 27, 2013   (JP) ................................ 2013-245427

(51) Int. Cl.
*A61B 6/00* (2006.01)
*A61B 5/0402* (2006.01)
*A61M 5/00* (2006.01)

(52) U.S. Cl.
CPC ............. *A61B 6/481* (2013.01); *A61B 5/0402* (2013.01); *A61B 6/486* (2013.01); *A61B 6/504* (2013.01); *A61M 5/007* (2013.01); *A61B 6/4441* (2013.01); *A61B 6/5205* (2013.01); *A61B 6/541* (2013.01); *A61M 2205/33* (2013.01)

(58) Field of Classification Search
CPC ......... A61B 6/481; A61B 6/486; A61B 6/504; A61B 6/4441; A61B 6/541; A61B 5/0402; A61M 5/007; A61M 2205/33
See application file for complete search history.

(56) References Cited

U.S. PATENT DOCUMENTS

2006/0235297 A1* 10/2006 Kawamoto ............ A61B 6/481
                                                                    600/431
2008/0240355 A1* 10/2008 Ohishi ................. A61B 6/4441
                                                                    378/98

(Continued)

FOREIGN PATENT DOCUMENTS

JP        05-207996 A      8/1993
JP        2001-149360 A    6/2001

(Continued)

OTHER PUBLICATIONS

International Search Report issued Jan. 28, 2014 in PCT/JP2013/081976 filed Nov. 27, 2013.

*Primary Examiner* — Catherine Voorhees
(74) *Attorney, Agent, or Firm* — Oblon, McClelland, Maier & Neustadt, L.L.P.

(57) ABSTRACT

An X-ray diagnostic apparatus according to an embodiment includes a processing circuitry. The processing circuitry configured to acquire blood flow state information indicating a blood flow state in a blood vessel of a subject, and control at least one of an injection start, an injection speed, and an injection amount of injection of a contrast media into the subject by an injector based on the blood flow state information acquired.

12 Claims, 10 Drawing Sheets

(56) References Cited

U.S. PATENT DOCUMENTS

2010/0046710 A1     2/2010   Ohishi
2010/0292570 A1    11/2010   Tsukagoshi
2012/0229504 A1     9/2012   Nakamura et al.

FOREIGN PATENT DOCUMENTS

| JP | 2006-141497 A | 6/2006 |
| JP | 2008-272454 A | 11/2008 |
| JP | 2010-005480 A | 1/2010 |
| JP | 2010-264185 A | 11/2010 |
| JP | 2012-147934 A | 8/2012 |

\* cited by examiner

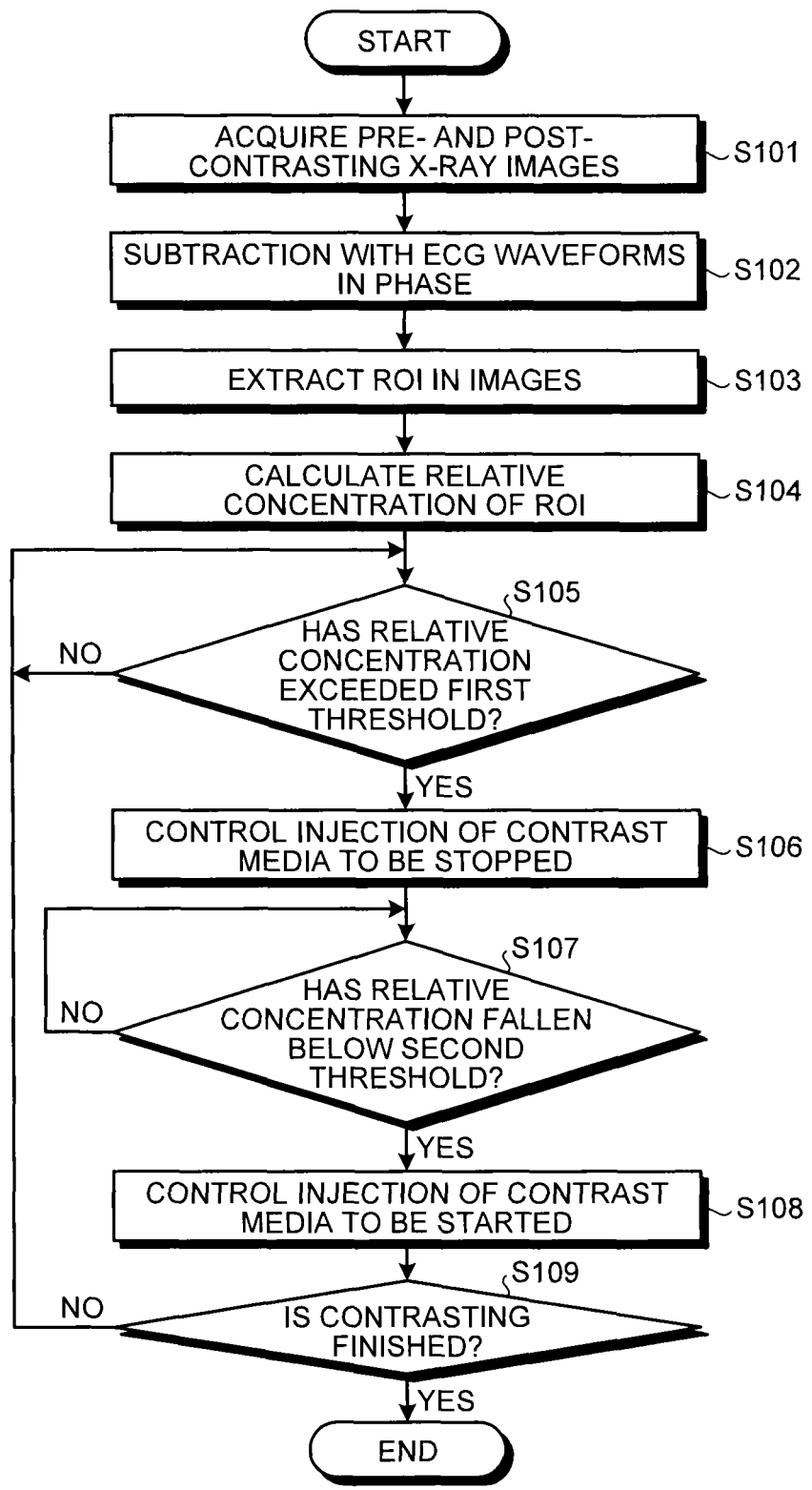

X-RAY DIAGNOSTIC APPARATUS AND INJECTOR

CROSS-REFERENCE TO RELATED APPLICATIONS

This application is a continuation-in-part (CIP) of PCT international application Ser. No. PCT/JP2013/081976 filed on Nov. 27, 2013 which designates the United States, incorporated herein by reference, and which claims the benefit of priority from Japanese Patent Application No. 2012-259022, filed on Nov. 27, 2012 and Japanese Patent Application No. 2013-245427, filed on Nov. 27, 2013, the entire contents of which are incorporated herein by reference.

FIELD

Embodiments described herein relate generally to an X-ray diagnostic apparatus and an injector.

BACKGROUND

Attention is conventionally paid to a Hybrid procedure that employs radiography with an X-ray diagnostic apparatus. The Hybrid procedure is a treatment by a procedure that uses both of a catheter procedure and a surgical procedure and is applied, for example, to a treatment of a great artery of a heart (such as an aortic aneurysm treatment or a valve replacement). When the Hybrid procedure is performed, the radiography is performed to confirm the shape of a blood vessel or a valve, the state thereof, and the like with a contrast media being injected thereinto.

When the Hybrid procedure is applied to the treatment of a great artery of the heart, the amount of the contrast media injected into a subject may be increased because the great artery of the heart is large and the blood flow therein is rapid. However, the amount of the contrast media to be used for one examination is limited depending on the weight, disease, presence of a renal dysfunction, and the like of the subject. Therefore, under a situation where the Hybrid procedure is applied to the treatment of a great artery of the heart and the like, it is desirable to suppress the used amount of the contrast media. In recent years, a technique that enables to suppress the used amount of a contrast media according to information of an image is known. However, in some cases, it is difficult for the conventional technique to appropriately suppress the used amount of a contrast media.

BRIEF DESCRIPTION OF THE DRAWINGS

FIG. 7 is a flowchart of a process procedure performed by the X-ray diagnostic apparatus according to the first embodiment;

DETAILED DESCRIPTION

According to an embodiment, an X-ray diagnostic apparatus includes processing circuitry. The processing circuitry configured to acquire blood flow state information indicating a blood flow state in a blood vessel of a subject, and control at least one of an injection start, an injection speed, and an injection amount of injection of a contrast media into the subject by an injector based on the blood flow state information acquired by the acquisition unit.

First Embodiment

Figure 1:
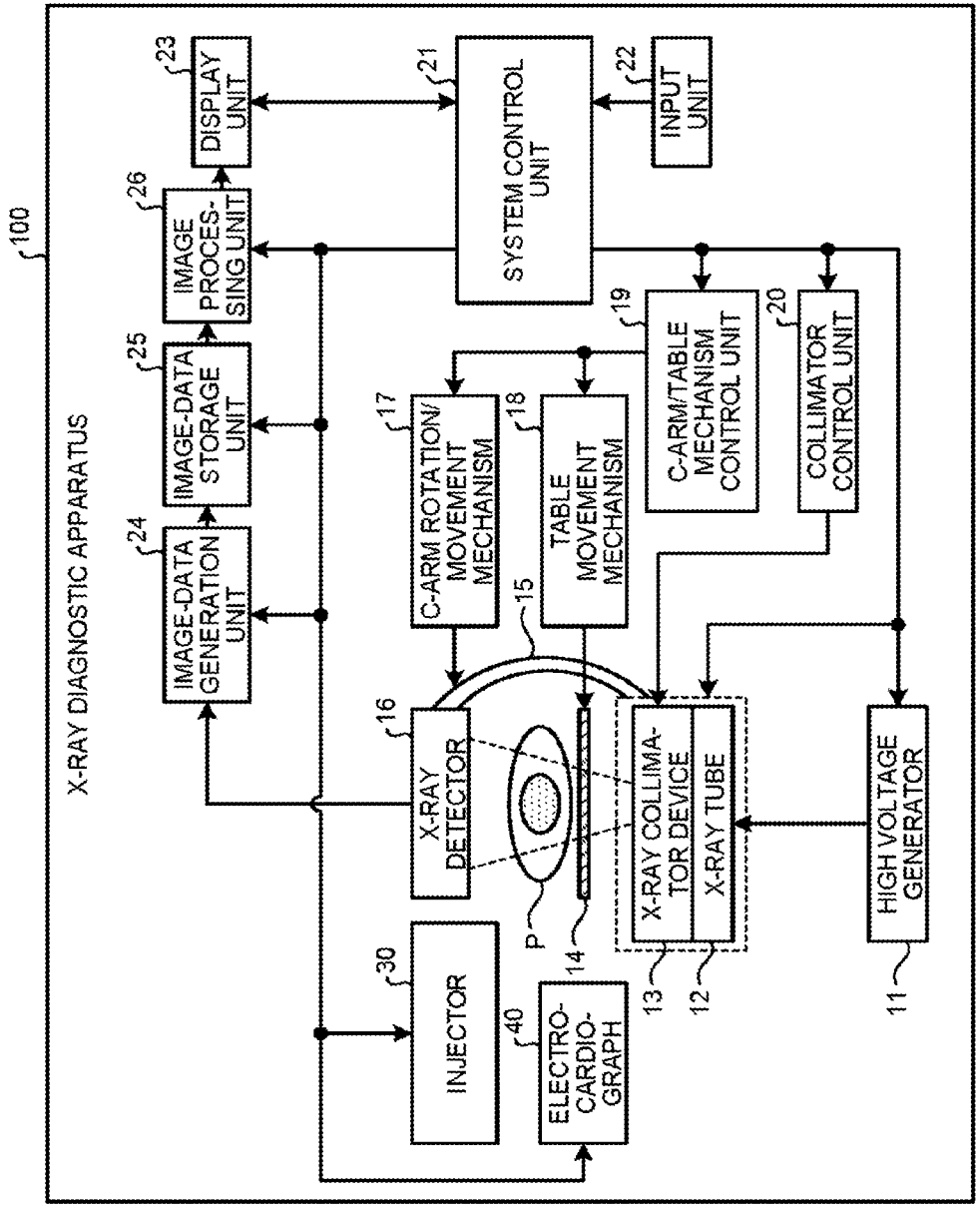
FIG. 1 is an example of a configuration of an X-ray diagnostic apparatus according to a first embodiment.

FIG. 1 is an example of a configuration of an X-ray diagnostic apparatus according to a first embodiment. As shown in FIG. 1, an X-ray diagnostic apparatus 100 according to the first embodiment includes a high voltage generator 11, an X-ray tube 12, an X-ray collimator device 13, a table 14, a C-arm 15, and an X-ray detector 16. The X-ray diagnostic apparatus 100 according to the first embodiment also includes a C-arm rotation/movement mechanism 17, a table movement mechanism 18, a C-arm/table mechanism control unit 19, a collimator control unit 20, a system control unit 21, an input unit 22, and a display unit 23. The X-ray diagnostic apparatus 100 according to the first embodiment further includes an image-data generation unit 24, an image-data storage unit 25, and an image processing unit 26. The X-ray diagnostic apparatus 100 is connected to an injector 30 and an electrocardiograph 40.

The injector 30 is a device that injects a contrast media through a catheter inserted into a subject P. Injection of the contrast media from the injector 30 is performed according to an injection instruction received via the system control unit 21 explained later. Specifically, the injector 30 performs injection of the contrast media according to an injection start instruction and an injection stop instruction for the contrast media received from the system control unit 21 explained later, and a contrast media injection condition including an injection speed. The injector 30 can execute an injection start or an injection stop according to an injection instruction input directly to the injector 30 by an operator.

The electrocardiograph 40 acquires an electrocardiogram (ECG) of the subject P to which a terminal (not shown) is attached, and sends the acquired ECG to the image-data generation unit 24 and the image processing unit 26 together with time information.

The high voltage generator 11 generates a high voltage under a control by the system control unit 21 and supplies the generated high voltage to the X-ray tube 12. The X-ray tube 12 generates X-rays using the high voltage supplied from the high voltage generator 11.

The X-ray collimator device 13 focuses the X-rays generated by the X-ray tube 12 to be selectively irradiated on an ROI of the subject P under a control by the collimator control unit 20. For example, the X-ray collimator device 13 has four slidable collimator blades. The X-ray collimator device 13 slides the collimator blades under the control by the collimator control unit 20, thereby focusing the X-rays generated by the X-ray tube 12 to irradiate the X-rays to the subject P. The table 14 is a bed on which the subject P is mounted and is placed on a bedstead (not shown). The subject P is not included in the X-ray diagnostic apparatus 100.

The X-ray detector 16 detects the X-rays transmitted through the subject P. For example, the X-ray detector 16 has detection elements arrayed in a matrix. Each of the detection elements converts the X-rays transmitted through the subject P into an electric signal, accumulates the electric signals therein, and sends the accumulated electric signals to the image-data generation unit 24.

The C-arm 15 holds the X-ray tube 12, the X-ray collimator device 13, and the X-ray detector 16. The X-ray tube 12 and the X-ray collimator device 13 are arranged by the C-arm 15 to face the X-ray detector 16 across the subject P.

The C-arm rotation/movement mechanism 17 is a mechanism that rotates and moves the C-arm 15 and the table movement mechanism 18 is a mechanism that moves the table 14. The C-arm/table mechanism control unit 19 controls the C-arm rotation/movement mechanism 17 and the table movement mechanism 18 to adjust rotation and movement of the C-arm 15 and movement of the table 14 under a control by the system control unit 21. The collimator control unit 20 adjusts an opening degree of the collimator blades of the X-ray collimator device 13 to control the irradiation range of the X-rays irradiated on the subject P under a control of the system control unit 21.

The image-data generation unit 24 generates image data using the electric signals converted from the X-rays by the X-ray detector 16, and stores the generated image data in the image-data storage unit 25. For example, the image-data generation unit 24 performs current/voltage conversion, A (Analog)/D (Digital) conversion, or parallel/serial conversion of the electric signals received from the X-ray detector 16 to generate image data.

The image-data generation unit 24 generates a plurality of X-ray images of the heart of the subject P to which the contrast media has been injected, captured according to time series. The image-data generation unit 24 then stores the generated X-ray images in the image-data storage unit 25. At this time, the image-data generation unit 24 according to the present embodiment stores the generated X-ray images in the image-data storage unit 25 while having the X-ray images being associated with the electrocardiogram and the time information received from the electrocardiograph 40.

The image-data storage unit 25 stores therein the image data generated by the image-data generation unit 24. For example, the image-data storage unit 25 stores therein image data of a predetermined region of the subject P to which the contrast media has been injected, captured according to time series. For example, the image-data storage unit 25 stores therein the X-ray images generated by the image-data generation unit 24 to be associated with capturing times and electrocardiograms at the capturing times, respectively.

The image processing unit 26 performs various kinds of image processing for the image data stored in the image-data storage unit 25. For example, the image processing unit 26 processes the X-ray images according to time series, stored in the image-data storage unit 25, thereby generating a moving image.

The input unit 22 receives various kinds of instructions from an operator such as a doctor or a technician that operates the X-ray diagnostic apparatus 100. For example, the input unit 22 has a mouse, a keyboard, a button, a trackball, or a joystick. The input unit 22 transfers the instruction received from the operator to the system control unit 21. For example, the input unit 22 receives a designation instruction for designating an arbitrary region in an X-ray image.

The display unit 23 displays a GUI (Graphical User Interface) for receiving instructions of the operator, the image data stored in the image-data storage unit 25, and the like. For example, the display unit 23 has a monitor. The display unit 23 can have a plurality of monitors.

The system control unit 21 controls the entire operation of the X-ray diagnostic apparatus 100. For example, the system control unit 21 controls the high voltage generator 11 according to an instruction of the operator, transferred from the input unit 22, to adjust a voltage supplied to the X-ray tube 12, thereby controlling an X-ray dose irradiated on the subject P or ON/OFF of X-ray irradiation. For example, the system control unit 21 also controls the C-arm/table mechanism control unit 19 according to an instruction of the operator to adjust rotation or movement of the C-arm 15 and movement of the table 14. For example, the system control unit 21 also controls the collimator control unit 20 according to an instruction of the operator to adjust the opening degree of the collimator blades of the X-ray collimator device 13, thereby controlling the irradiation range of the X-rays irradiated on the subject P.

The system control unit 21 also controls an image-data generation process performed by the image-data generation unit 24, image processing by the image processing unit 26, analysis processing, and the like according to an instruction of the operator. The system control unit 21 executes a control to display the GUI for receiving instructions of the operator or the images stored in the image-data storage unit 25 on the monitor of the display unit 23. The system control unit 21 sends a signal of a start or stop of the contrast media injection to the injector 30, thereby controlling an injection timing of the contrast media.

The X-ray diagnostic apparatus 100 according to the present embodiment can appropriately suppress the used amount of the contrast media. Specifically, the X-ray diagnostic apparatus 100 determines the concentration of the contrast media based on a blood flow state in a blood vessel and controls the injector according to a process performed by the system control unit 21, which is explained below in detail, thereby appropriately suppressing the used amount of the contrast media.

For example, when a great artery of the heart is to be contrasted, a larger amount of the contrast media is used for one contrasting than in a coronary artery or a cerebral blood vessel because the great artery is a region where the blood vessel is large and the blood flow is rapid. As an example, when a great artery is to be contrasted, 15 to 20 milliliters of the contrast media is used for one contrasting in some cases. As mentioned above, the used amount of the contrast media for one examination is limited depending on the weight, disease, and presence of a renal dysfunction, and the like of a subject and is required to be, for example, equal to or lower than 100 milliliters in one examination. Therefore, for example, when 20 milliliters are used for one contrasting, the used amount reaches the limit at the time of the fourth or fifth contrasting.

In recent years, a stent-graft insertion technique is established, for example, as a treatment method for an aortic aneurysm disease. In such a treatment method, it is required to suppress the amount of the contrast media used for one contrasting and to increase the number of times of contrasting as much as possible to perform indwelling of a stent graft or confirmation of presence of an endoleak.

Figure 2:
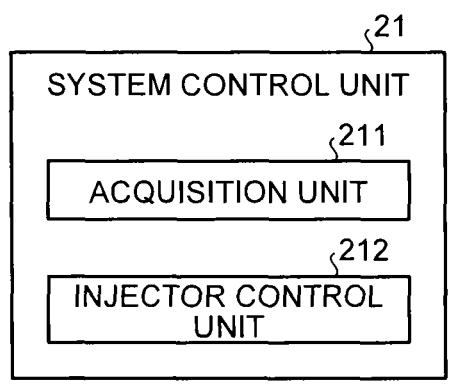
FIG. 2 is an example of a configuration of a system control unit according to the first embodiment.

The X-ray diagnostic apparatus 100 according to the present application determines the concentration of the contrast media based on a blood flow state in a blood vessel and controls the injector, thereby appropriately suppressing the used amount of the contrast media. FIG. 2 is an example of a configuration of the system control unit 21 according to the first embodiment. As shown in FIG. 2, the system control unit 21 according to the first embodiment has an acquisition unit 211 and an injector control unit 212.

The acquisition unit 211 acquires blood flow state information indicating a blood flow state in a blood vessel of a subject. Specifically, the acquisition unit 211 acquires a signal value of a predetermined region included in an X-ray image as the blood flow state information. For example, the acquisition unit 211 acquires a difference between signal values of predetermined regions included in an X-ray image, thereby acquiring a relative concentration of the contrast media between the predetermined regions. The acquisition unit 211 according to the first embodiment can acquire the blood flow state information using a plurality of acquisition methods. The acquisition methods of the blood flow state information performed by the acquisition unit 211 are explained in turn below.

Figure 3A:
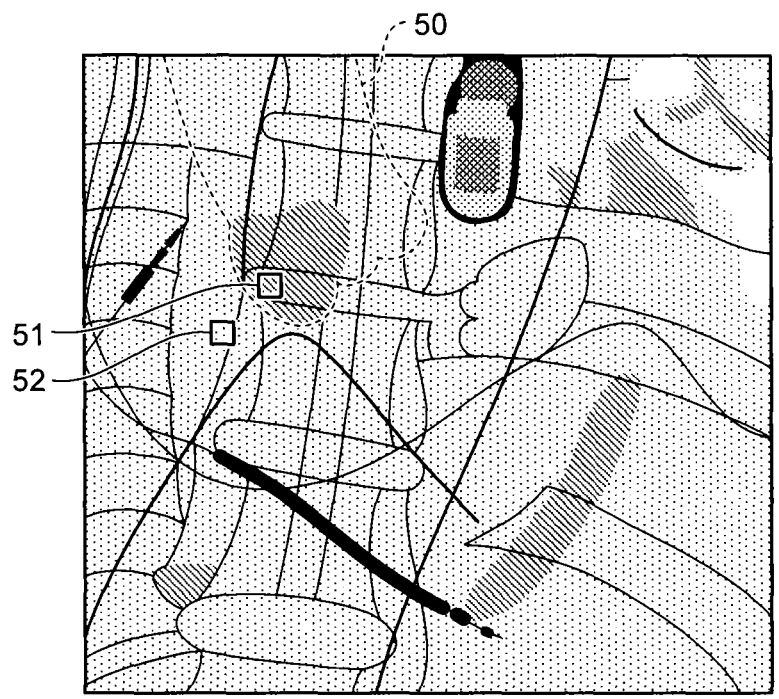
FIG. 3A is an explanatory diagram of a first example of a process performed by an acquisition unit according to the first embodiment.

A first example is explained first. For example, the acquisition unit 211 acquires a difference between signal values of a first region included in a blood vessel region of an X-ray image and a second region included in a non-blood vessel region of the X-ray image, thereby acquiring a relative concentration between the regions. FIG. 3A is an explanatory diagram of a first example of a process performed by the acquisition unit 211 according to the first embodiment. FIG. 3A shows one frame of X-ray images of an aorta 50 including an aortic valve, captured with times while the contrast media is injected thereinto.

For example, as shown in FIG. 3A, the acquisition unit 211 reads each of the X-ray images generated in a time-series order by the image-data generation unit 24, from the image-data storage unit 25 and acquires a difference between an region 51 and an region 52 of the read image data to calculate a contrast media concentration. The regions 51 and 52 in this example are explained. The regions 51 and 52 are a region set in a blood vessel region and a region set in a non-blood vessel region, respectively.

These regions can be set by a user or can be automatically extracted by the acquisition unit 211. When the regions are to be set by a user, the user sets the region 51, for example, by clicking an arbitrary position in a blood vessel region with a mouse to designate a point or by dragging the mouse to designate a range. Similarly, the user sets the region 52 by clicking an arbitrary position or dragging the mouse in a non-blood vessel region.

Meanwhile, when the regions are to be automatically extracted by the acquisition unit 211, the acquisition unit 211 first acquires a pre-contrasting X-ray image and a post-contrasting X-ray image from the X-ray image data captured with times and performs a differentiating process (subtraction), thereby extracting a contrasted region. That is, the acquisition unit 211 extracts an region left after the subtraction (a contrasted region) as a blood vessel region. At this time, the acquisition unit 211 acquires the pre- and post-contrasting X-ray images having the same phase by referring to ECG waveforms associated with the X-ray image data captured with times, respectively. In this way, the subtraction can be performed at substantially the same positions of the subject even in a case where the subtraction is performed to the pre- and post-contrasting X-ray images. In other words, the acquisition unit 211 aligns images and then performs the subtraction. In the subtraction, the same process as in the subtraction between the regions 51 and 52 explained later is performed.

The acquisition unit 211 can extract the blood vessel region and the non-blood vessel region by performing the subtraction of the pre- and post-contrasting X-ray images. The acquisition unit 211 further extracts, from the blood vessel region extracted by the subtraction, a boundary with the non-blood vessel region as a blood-vessel periphery region. That is, the acquisition unit 211 can distinguish the blood-vessel periphery region from the inside region of the blood vessel region and extract the distinguished blood-vessel periphery region. The user can arbitrarily set where the blood-vessel periphery region starting from the boundary with the non-blood vessel region in the blood vessel region ends.

As described above, the acquisition unit 211 calculates a concentration difference (a contrast media concentration) by subtracting the region 52 (the region in the non-blood vessel region) from the region 51 (the region in the blood vessel region) set by the user or automatically extracted. For example, the acquisition unit 211 obtains a difference of pixel values of pixels included in the regions 51 and 52 between corresponding pixels (pixels at the same position) and calculates an accumulated value of the obtained differences as the concentration difference.

The acquisition unit 211 performs the subtraction of the region 52 from the region 51 in each of the X-ray images in which the contrast media is injected and which are captured with times to calculate the contrast media concentration of the region 51 in each phase. That is, the acquisition unit 211 acquires information of the contrast media concentration (information indicating the blood vessel state) in the blood vessel after injection of the contrast media.

Referring back to FIG. 2, the injector control unit 212 controls injection of the contrast media into the subject by the injector based on the blood flow state information acquired by the acquisition unit 211. Specifically, the injector control unit 212 controls at least one of an injection start, an injection speed, and an injection amount of the injection of the contrast media into the subject by the injector according to changes in the signal value (changes in the relative concentration of the contrast media) acquired by the acquisition unit 211. More specifically, the injector control unit 212 controls a contrast media injection condition including timings of the start and stop of the injection of the contrast media by the injector 30 and the injection speed of the contrast media based on the blood flow state information acquired by the acquisition unit 211.

Figure 3B:
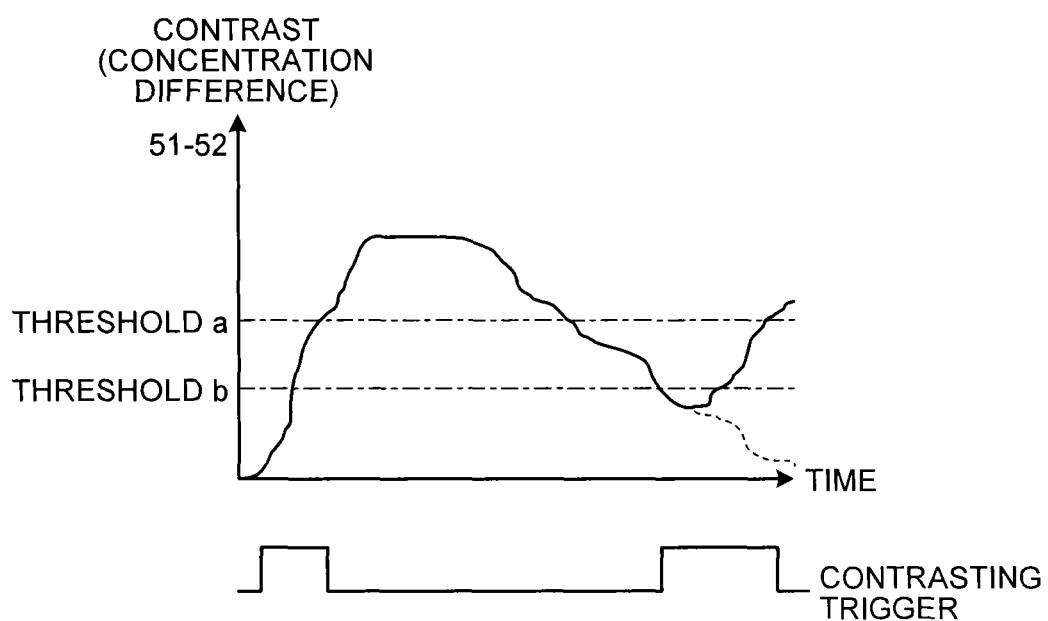
FIG. 3B is an explanatory diagram of a first example of a process performed by an injector control unit according to the first embodiment.

FIG. 3B is an explanatory diagram of a first example of a process performed by the injector control unit 212 according to the first embodiment. In FIG. 3B, a graph representing the time on the horizontal axis and the concentration difference of the region 52 from the region 51 on the vertical axis, and a chart representing the time on the horizontal axis and ON/OFF of the injector on the vertical axis are depicted on upper and lower sides thereof, respectively.

For example, as shown by the graph on the upper side of FIG. 3B, the concentration difference calculated by the acquisition unit 211 increases to reach a peak and gradually decreases with the time. This shows a state where the contrast media concentration in the region 51 is increased by injection of the contrast media and then the contrast media concentration is decreased by gradual flowing of the contrast media out of the region 51.

For example, the injector control unit 212 controls the injection start and the injection stop of the contrast media by performing a concentration determination with thresholds "a" and "b" set for the concentration differences, as shown by the chart on the lower side of FIG. 3B. That is, the injector control unit 212 controls injection of the contrast media from the injector to be stopped when the concentration difference between the regions 51 and 52 exceeds the threshold "a". The injector control unit 212 controls injection of the contrast media from the injector to be started when the concentration difference between the regions 51 and 52 falls below the threshold "b" as shown in FIG. 3B.

In this way, by controlling the injection start and the injection stop of the contrast media with reference to the relative concentration of the contrast media between the blood vessel region and the non-blood vessel region in an X-ray image, the used amount of the contrast media can be appropriately suppressed regardless of imaging conditions.

A case where two thresholds are used has been explained in the example of FIG. 3B. However, the embodiment is not limited thereto and, for example, the injection start and the injection stop of the contrast media can be controlled using one threshold.

A case where the injection start and the injection stop of the contrast media are controlled has been explained in the example of FIG. 3B. However, the embodiment is not limited thereto and, for example, the injection speed of the contrast media or the like can be controlled. In such a case, the injector control unit 212, for example, calculates the speed at which the concentration difference increases (the inclination of rising of the graph) with reference to the graph on the upper side of FIG. 3B. The injector control unit 212 then decides the injection rate (ml/s) of the contrast media based on the calculated speed and controls the injector to inject the contrast media at the decided injection rate.

Figure 4A:
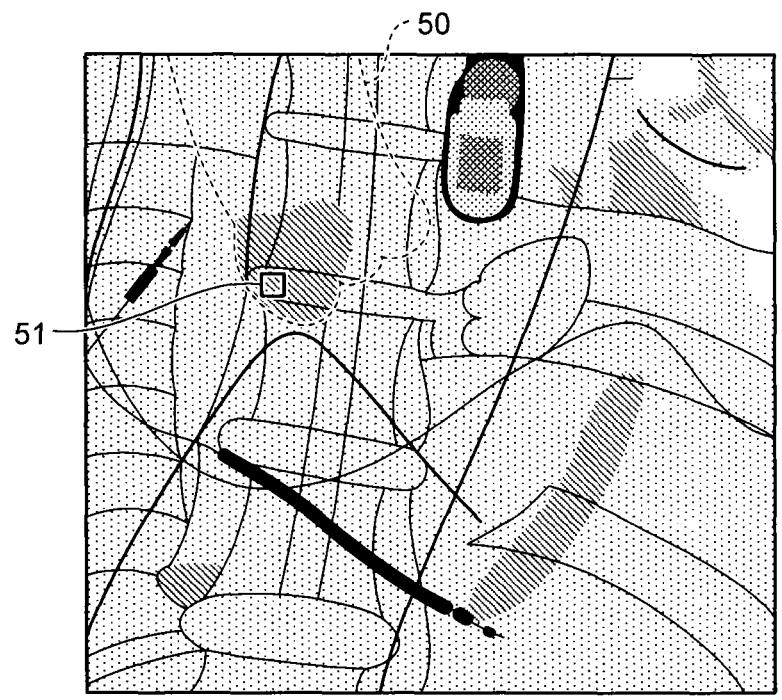
FIG. 4A is an explanatory diagram of a second example of the process performed by the acquisition unit according to the first embodiment.

In the first example mentioned above, a case where the concentration difference between a region in the blood vessel region and a region in the non-blood vessel region is calculated has been explained. A second example where a concentration difference of a region in the blood vessel region between before and after contrasting is calculated is explained next. For example, the acquisition unit 211 acquires a relative concentration between before and after contrasting of the blood vessel region of an X-ray image. FIG. 4A is an explanatory diagram of a second example of a process performed by the acquisition unit 211 according to the first embodiment. FIG. 4A shows one frame of X-ray images of the aorta 50 including an aortic valve, captured with times while the contrast media is injected thereinto.

For example, the acquisition unit 211 reads a pre-contrasting X-ray image and a post-contrasting X-ray image from the X-ray images generated in a time-series order by the image-data generation unit 24 and stored by the image-data storage unit 25 as shown in FIG. 4A. The acquisition unit 211 performs the subtraction between the region 51 in the post-contrasting X-ray image and the region 51 in the pre-contrasting X-ray image to calculate the contrast media concentration. The region 51 in FIG. 4A is a region set in the blood vessel region, similarly to the region 51 in FIG. 3A. The region 51 in FIG. 4A can be set by a user or automatically extracted by the acquisition unit 211, as mentioned above.

The acquisition unit 211 reads post-contrasting X-ray images stored in the image-data storage unit 25, in a time-series order and sequentially performs the subtraction between the region 51 in each of the X-ray images and the region 51 in a pre-contrasting X-ray image previously read to calculate the contrast media concentration in each phase. The subtraction between before and after contrasting is performed with the phases aligned using the ECG waveforms. That is, a pre-contrasting X-ray image in substantially the same phase as that of each of the post-contrasting X-ray images is extracted and the subtraction between the regions 51 in the X-ray images is performed.

Figure 4B:
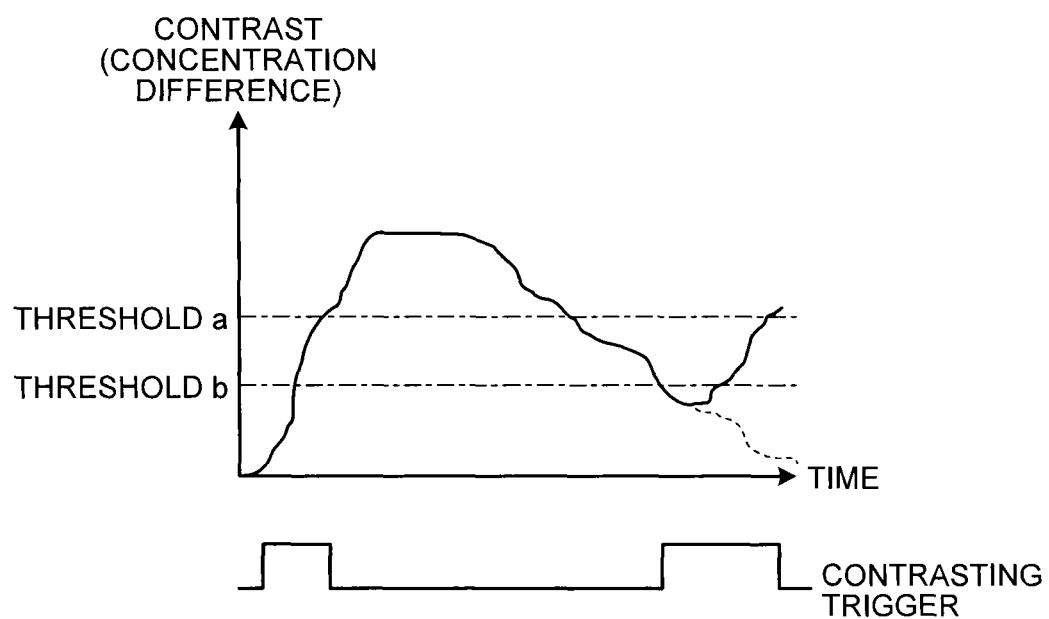
FIG. 4B is an explanatory diagram of a second example of the process performed by the injector control unit according to the first embodiment.

FIG. 4B is an explanatory diagram of a second example of a process performed by the injector control unit 212 according to the first embodiment. In FIG. 4B, a graph representing the time on the horizontal axis and the concentration difference in the region 51 between before and after contrasting on the vertical axis, and a chart representing the time on the horizontal axis and ON/OFF of the injector on the vertical axis are depicted on upper and lower sides thereof, respectively.

For example, as shown by the graph on the upper side of FIG. 4B, the concentration difference calculated by the acquisition unit 211 increases to reach a peak and gradually decreases with the time. This shows a state where the contrast media concentration in the region 51 is increased by injection of the contrast media and the contrast media concentration is decreased by gradual flowing of the contrast media out of the region 51, similarly in FIG. 3A.

For example, the injector control unit 212 controls the injection start and the injection stop of the contrast media by performing a concentration determination with the thresholds "a" and "b" set for the concentration differences, as shown by the chart on the lower side of FIG. 4B. That is, the injector control unit 212 controls injection of the contrast media from the injector to be stopped when the concentration difference in the region 51 between before and after contrasting exceeds the threshold "a". The injector control unit 212 controls injection of the contrast media from the injector to be started when the concentration difference in the region 51 between before and after contrasting falls below the threshold "b", as shown in FIG. 4B.

This enables to appropriately suppress the used amount of the contrast media only using a region in a blood vessel. Also in the second embodiment mentioned above, FIGS. 4A and 4B are merely an example and the embodiment is not limited thereto. That is, the number of thresholds and the control target of the injector (the injection speed of the contrast media, for example) can be arbitrarily changed.

A third example is explained next. In the first and second examples, a case where the concentration difference in one region set in the blood vessel region is calculated to control the injector has been explained. In the third example, a case where a plurality of regions are set in a blood vessel region and the injector is controlled according to concentrations in the regions is explained.

Figure 5A:
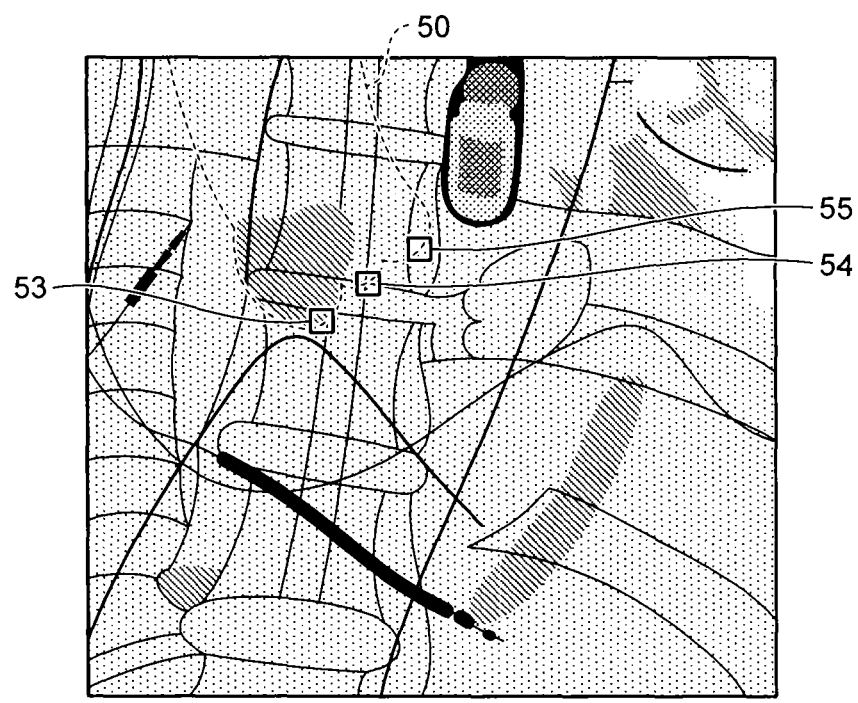
FIG. 5A is an explanatory diagram of a third example of the process performed by the acquisition unit according to the first embodiment.

FIG. 5A is an explanatory diagram of a third example of a process performed by the acquisition unit 211 according to the first embodiment. FIG. 5A shows one frame of X-ray images of the aorta 50 including an aortic valve, captured with times while the contrast media is injected thereinto.

For example, the acquisition unit 211 reads a pre-contrasting X-ray image and a post-contrasting X-ray image from the X-ray image data generated in a time-series order by the image-data generation unit 24 and stored by the image-data storage unit 25, as shown in FIG. 5A. The acquisition unit 211 performs the subtraction between regions 53, 54, and 55 in the post-contrasting X-ray image and the regions 53, 54, and 55 in the pre-contrasting X-ray image, respectively, to calculate the contrast media concentrations in the regions. The regions 53, 54, and 55 in FIG. 5A are regions set in the blood vessel region. The regions 53, 54, and 55 in FIG. 5A can be set by a user or automatically extracted by the acquisition unit 211 as mentioned above.

The acquisition unit 211 reads post-contrasting X-ray images stored in the image-data storage unit 25 in a time-series order and sequentially performs the subtraction between the regions 53, 54, and 55 in each of the post-contrasting X-ray images and the regions 53, 54, and 55 in a pre-contrasting X-ray image previously read to calculate the contrast media concentrations in the regions in each phase, respectively. The subtraction between pre-contrasting and post-contrasting is performed with the phases aligned using the ECG waveforms. That is, a pre-contrasting X-ray image in substantially the same phase as that of each of the post-contrasting X-ray images is extracted and then the subtraction between the regions 53, 54, and 55 in the X-ray images is performed, respectively.

Figure 5B:
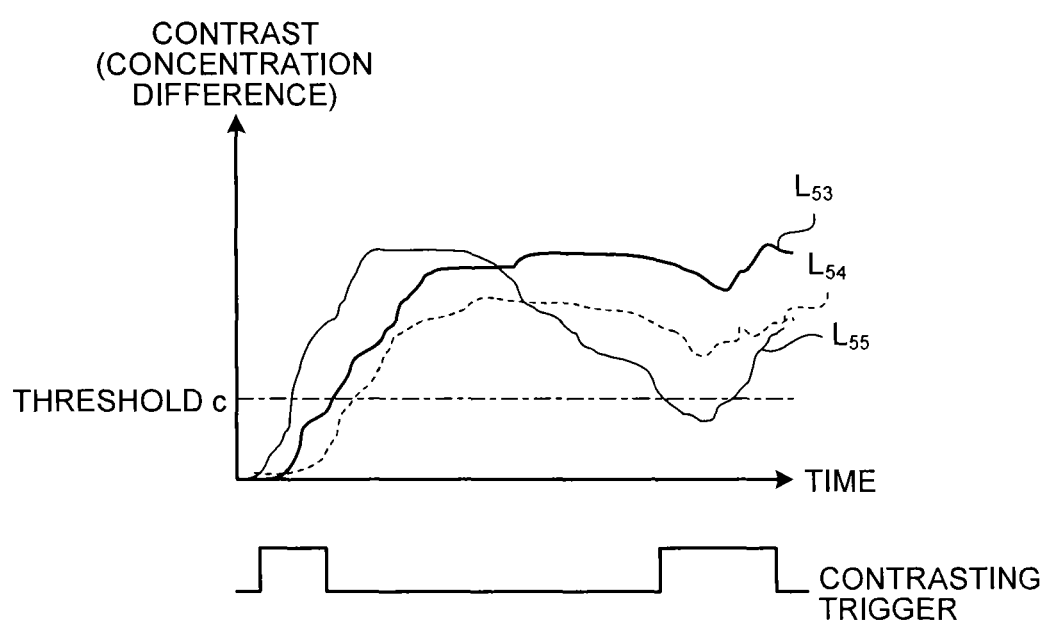
FIG. 5B is an explanatory diagram of a third example of the process performed by the injector control unit according to the first embodiment.

FIG. 5B is an explanatory diagram of a third example of a process performed by the injector control unit 212 according to the first embodiment. In FIG. 5B, graphs representing the time on the horizontal axis and the concentration differences in the regions 53, 54, and 55 between before and after contrasting on the vertical axis, respectively, and a chart representing the time on the horizontal axis and ON/OFF of the injector on the vertical axis are depicted on upper and lower sides thereof, respectively. $L_{53}$ in FIG. 5B is a graph indicating temporal changes of the concentration difference in the region 53, $L_{54}$ in FIG. 5B is a graph indicating temporal changes of the concentration difference in the region 54, and $L_{55}$ in FIG. 5B is a graph indicating temporal changes of the concentration difference in the region 55.

For example, as shown by the graphs on the upper side of FIG. 5B, the concentration differences in the regions calculated by the acquisition unit 211 increase to reach peaks and gradually decrease with the time, respectively. This shows a state where the contrast media concentrations in the regions are increased by injection of the contrast media and the contrast media concentrations are decreased by gradual flowing of the contrast media out of the regions, respectively, similarly in FIG. 3A. As shown in FIG. 5B, the temporal changes of the concentration differences in the regions differ. That is, this indicates that situations where the contrast media flows differ among regions in the same blood vessel.

For example, the injector control unit 212 controls the injection start and the injection stop of the contrast media by performing a concentration determination with a threshold "c" set for the concentration differences, as shown by the chart on the lower side of FIG. 5B. That is, the injector control unit 212 controls injection of the contrast media from the injector to be stopped when at least one of the concentration differences in the regions 53, 54, and 55 between before and after contrasting exceeds the threshold "c". The injector control unit 212 controls injection of the contrast media from the injector to be started when at least ones of the concentration differences in the regions 53, 54, and 55 between before and after contrasting falls below the threshold "c", as shown in FIG. 5B.

Accordingly, for example, even when a blood vessel is large as a great artery in the heart, the injector can be controlled in consideration of the flow status of the contrast media in the entire blood vessel. Also in the third example mentioned above, FIGS. 5A and 5B are merely an example and the embodiment is not limited thereto. That is, the number of thresholds and the control target of the injector (the injection speed of the contrast media, for example) can be arbitrary changed.

In the example of FIGS. 5A and 5B, a case where the concentration differences in the regions 53, 54, and 55 are calculated from the pre- and post-contrasting X-ray images of the regions, respectively, has been explained. However, the embodiment is not limited thereto and, for example, a region can be set in the non-blood vessel region to perform the subtraction between each of the regions 53, 54 and 55, and the region in the non-blood vessel region.

In the example of FIGS. 5A and 5B, a case where the injector is controlled when the concentration difference of one of three regions exceeds or falls below the threshold has been explained. However, the present embodiment is not limited thereto and conditions to control the injector can be arbitrary decided. For example, the injector can be controlled when the concentration differences of all the three regions exceed or fall below the threshold. The number of regions can be arbitrarily set and two regions can be used. Alternatively, four or more regions can be used.

A fourth example is explained next. In the third example, a case where the determination is performed using the same threshold for each of the regions has been explained. In the fourth embodiment, a case where different thresholds are set for the regions, respectively, (the regions are weighted) is explained.

Figure 6A:
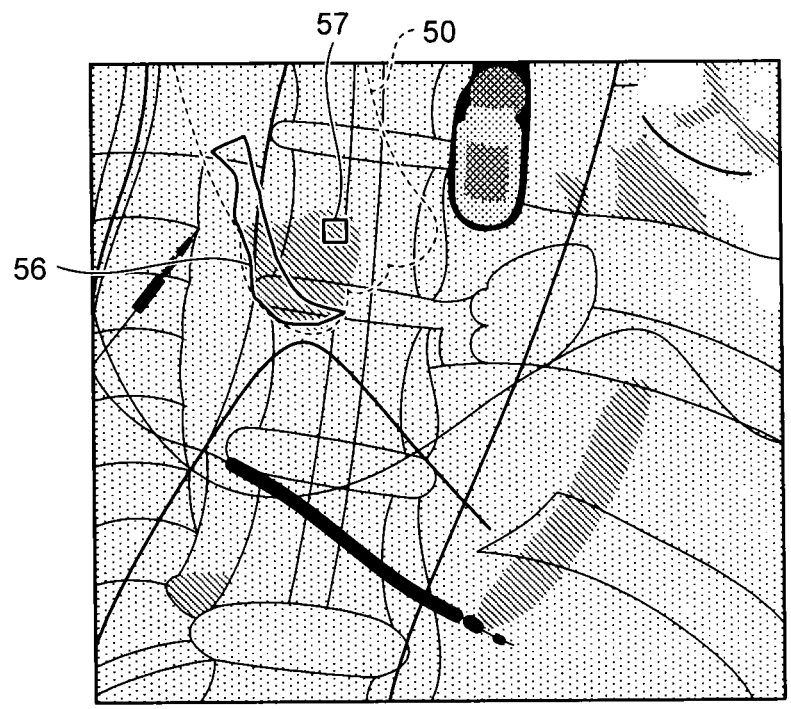
FIG. 6A is an explanatory diagram of a fourth example of the process performed by the acquisition unit according to the first embodiment.

FIG. 6A is an explanatory diagram of a fourth example of a process performed by the acquisition unit 211 according to the first embodiment. FIG. 6A shows one frame of X-ray images of the aorta 50 including an aortic valve, captured with times while the contrast media is injected thereinto.

For example, the acquisition unit 211 reads a pre-contrasting X-ray image and a post-contrasting X-ray image from the X-ray image data generated in a time-series order by the image-data generation unit 24 and stored by the image-data storage unit 25, as shown in FIG. 6A. The acquisition unit 211 performs the subtraction between regions 56 and 57 in the post-contrasting X-ray image and regions 56 and 57 in the pre-contrasting X-ray image to calculate contrast media concentrations in the regions, respectively. The region 56 in FIG. 6A is a blood vessel periphery and the region 57 is a region set in the blood vessel region. As mentioned above, the regions 56 and 57 in FIG. 6A can be set by a user or automatically extracted by the acquisition unit 211.

The acquisition unit 211 reads post-contrasting X-ray images stored in the image-data storage unit 25 in a time-series order and sequentially performs the subtraction between the regions 56 and 57 in each of the X-ray images and the regions 56 and 57 in a pre-contrasting X-ray image previously read to calculate contrast media concentrations of the regions in each phase, respectively. The subtraction between pre-contrasting and post-contrasting is performed with the phases aligned using the ECG waveforms. That is, a pre-contrasting X-ray image having substantially the same phase as that of each of the post-contrasting X-ray images is extracted and then the subtraction for each of the regions 56 and 57 in each of the X-ray images is performed.

Figure 6B:
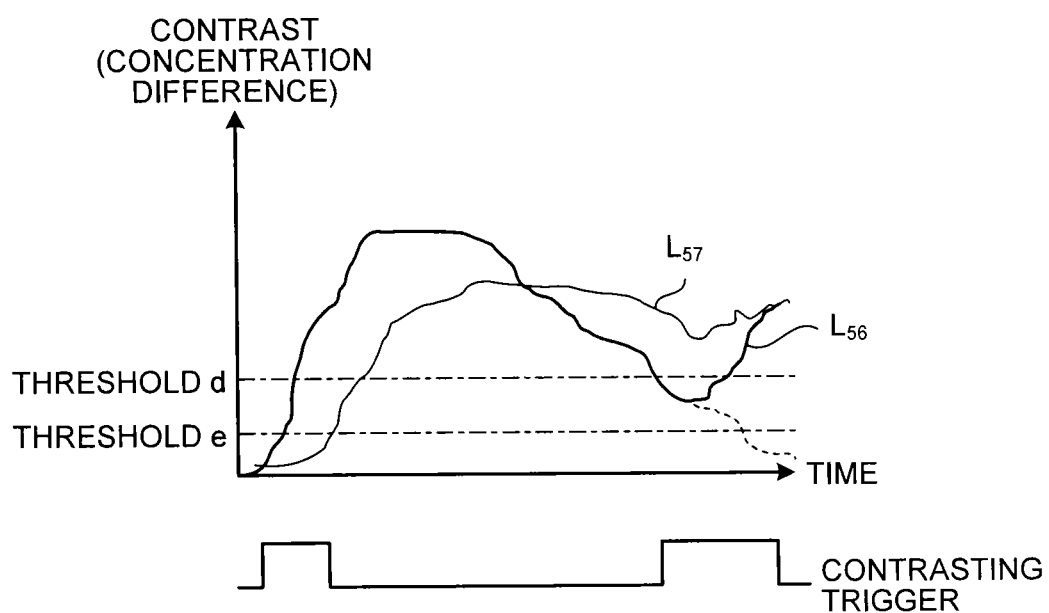
FIG. 6B is an explanatory diagram of a fourth example of the process performed by the injector control unit according to the first embodiment.

FIG. 6B is an explanatory diagram of a fourth example of a process performed by the injector control unit 212 according to the first embodiment. In FIG. 6B, graphs representing the time on the horizontal axis and the concentration differences between before and after contrasting in the regions 56 and 57 on the vertical axis, respectively, and a chart representing the time on the horizontal axis and ON/OFF of the injector on the vertical axis are depicted on upper and lower sides thereof, respectively. $L_{56}$ in FIG. 6B is a graph indicating temporal changes of the concentration difference in the region 56 and $L_{57}$ in FIG. 6B is a graph indicating temporal changes of the concentration difference in the region 57.

For example, as shown by the graphs on the upper side of FIG. 6B, the concentration differences of the regions calculated by the acquisition unit 211 increase to reach peaks and gradually decrease with the time, respectively. This shows a state where the contrast media concentrations of the regions are increased by injection of the contrast media and the contrast media concentrations are decreased by gradual flowing of the contract agent out of the regions, respectively, similarly in FIG. 3A. As shown in FIG. 6B, the temporal changes of the concentration differences in the regions differ. That is, this indicates that situations where the contrast media flows differ according to regions in the same blood vessel.

For example, the injector control unit 212 sets a threshold "d" for the concentration difference of the region 56 and sets a threshold "e" for the concentration difference of the region 57 to perform concentration determinations, thereby controlling the injection start and the injection stop of the contrast media, as shown by the chart on the lower side of FIG. 6B. That is, the injector control unit 212 controls injection of the contrast media from the injector to be stopped when the concentration difference of the region 56 between before and after contrasting exceeds the threshold "d". The injector control unit 212 controls injection of the contrast media from the injector to be started when the concentration difference of the region 56 between before and after contrasting falls below the threshold "d" as shown in FIG. 6B.

Similarly, the injector control unit 212 controls injection of the contrast media from the injector to be stopped when the concentration difference of the region 57 between before and after contrasting exceeds the threshold "e". The injector control unit 212 controls injection of the contrast media from the injector to be started when the concentration difference of the region 57 between before and after contrasting falls below the threshold "e" as shown in FIG. 6B.

As shown in FIG. 6B, the thresholds "d" and "e" have different values. That is, the injector is controlled by weighting the concentration differences of the regions. Accordingly, an region that is desired to be always contrasted such as a blood vessel periphery of the aorta and an region that is not so important such as the inside of a blood vessel can be separated and then the injector can be controlled according to changes in the contrast media concentrations of the regions.

In the example of FIGS. 6A and 6B, a case where the concentration differences of the regions 56 and 57 are calculated from pre- and post-contrasting X-ray images of the regions 56 and 57 has been explained. However, the present embodiment is not limited thereto and, for example, a region can be set in the non-blood vessel region and the subtraction between each of the regions 56 and 57 and the region in the non-blood vessel region can be performed.

A process performed by the X-ray diagnostic apparatus 100 according to the first embodiment is explained next with reference to FIG. 7. FIG. 7 is a flowchart of a process procedure performed by the X-ray diagnostic apparatus 100 according to the first embodiment. FIG. 7 shows a process performed after a contrast media is injected and then X-ray images are captured with times. In FIG. 7, a process of a case where the acquisition unit 211 automatically extracts a region in an X-ray image (referred to as "region of interest (ROI)") is shown.

As shown in FIG. 7, in the X-ray diagnostic apparatus 100 according to the first embodiment, the acquisition unit 211 acquires pre- and post-contrasting X-ray images (Step S101) and performs the subtraction between the pre- and post-contrasting X-ray images with the ECG waveforms in phase (Step S102). The acquisition unit 211 extracts an ROI in each of the images (Step S103).

The acquisition unit 211 then calculates a relative concentration of the ROI (Step S104) and the injector control unit 212 determines whether the relative concentration has exceeded a first threshold (Step S105). When the relative concentration has not exceeded the first threshold (NO at Step S105), the contrast media is continuously injected.

Meanwhile, when the relative concentration has exceeded the first threshold (YES at Step S105), the injector control unit 212 controls injection of the contrast media to be stopped (Step S106). The injector control unit 212 then determines whether the relative concentration has fallen below a second threshold (Step S107). When the relative concentration has not fallen below the second threshold (NO at Step S107), the injection of the contrast media is continuously stopped.

On the other hand, when the relative concentration has fallen below the second threshold (YES at Step S107), the injector control unit 212 controls injection of the contrast media to be started (Step S108). The system control unit 21 then determines whether contrasting is finished (Step S109). When the contrasting is finished (YES at Step S109), the injector control unit 212 finishes the process. When the contrasting is not finished (NO at Step S109), the injector control unit 212 returns to Step S105 to perform determinations with the thresholds.

The first and second thresholds in FIG. 7 can be the same or difference values, respectively. While the case where the acquisition unit 211 extracts the ROI is shown in FIG. 7, the X-ray diagnostic apparatus 100 according to the first embodiment can receive region information from a user. In such a case, a determination process of determining whether a region is set is performed at Step S102 in FIG. 7.

As described above, according to the first embodiment, the acquisition unit 211 acquires blood flow state information indicating a blood flow state in a blood vessel of a subject. The injector control unit 212 controls at least one of the injection start, the injection speed, and the injection amount of injection of the contrast media into the subject by the injector based on the blood flow state information acquired by the acquisition unit 211. Therefore, the X-ray diagnostic apparatus 100 according to the first embodiment can determine a flow situation of the contract agent in the blood vessel and control the injection of the contrast media by the injector, thereby suppressing the used amount of the contrast media appropriately.

According to the first embodiment, the acquisition unit 211 acquires the relative concentration of the contrast media in a predetermined region included in each of the X-ray images as the blood flow state information. The injector control unit 212 controls at least one of the injection start, the injection speed, and the injection amount of injection of the contrast media into the subject by the injector 30 according to changes of a signal value (changes of the relative concentration of the contrast media) acquired by the acquisition unit 211. Therefore, the X-ray diagnostic apparatus 100 according to the first embodiment can determine the contrast media concentration without being affected, for example, by the body thickness of the subject or examination situations, thereby suppressing the used amount of the contrast media more appropriately.

According to the first embodiment, the acquisition unit 211 acquires signal values (the relative concentrations of the contrast media) in regions included in each of the X-ray images, respectively. The injector control unit 212 changes the control on the injection of the contrast media into the subject by the injector corresponding to changes in the relative concentrations of the contrast media according to importance degrees of the regions. Therefore, the X-ray diagnostic apparatus 100 according to the first embodiment can accurately contrast an important region such as a blood vessel periphery.

According to the first embodiment, the acquisition unit 211 acquires a difference of signal values between a first region included in the blood vessel region of an X-ray image and a second region included in the non-blood vessel region of the X-ray image. The injector control unit 212 executes a control according to changes in the difference of the signal values acquired by the acquisition unit 211. Therefore, the X-ray diagnostic apparatus 100 according to the first embodiment can accurately calculate the contrast media concentration.

According to the first embodiment, the acquisition unit acquires a difference of signal values of a blood vessel region of an X-ray image between before and after contrasting. The injector control unit 212 executes a control according to changes in the difference of signal values acquired by the acquisition unit 211. Therefore, the X-ray diagnostic apparatus 100 according to the first embodiment can accurately calculate the contrast media concentration using a single region, which enables to easily perform appropriate suppression of the used amount of the contrast media.

According to the first embodiment, the acquisition unit 211 extracts the blood vessel region from X-ray images before and after contrasting using the contrast media. Therefore, the X-ray diagnostic apparatus 100 according to the first embodiment can avoid a trouble of a user.

According to the first embodiment, the injector control unit 212 controls timings of the start and the stop of the injection of the contrast media by the injector 30 and a contrast media injection condition including the injection speed of the contrast media based on the blood flow state information acquired by the acquisition unit 211. Therefore, the X-ray diagnostic apparatus 100 according to the first embodiment can finely control the injection of the contrast media by the injector.

Second Embodiment

While the first embodiment has been described above, the present application can be carried out by various other modes other than the first embodiment.

Figure 8:
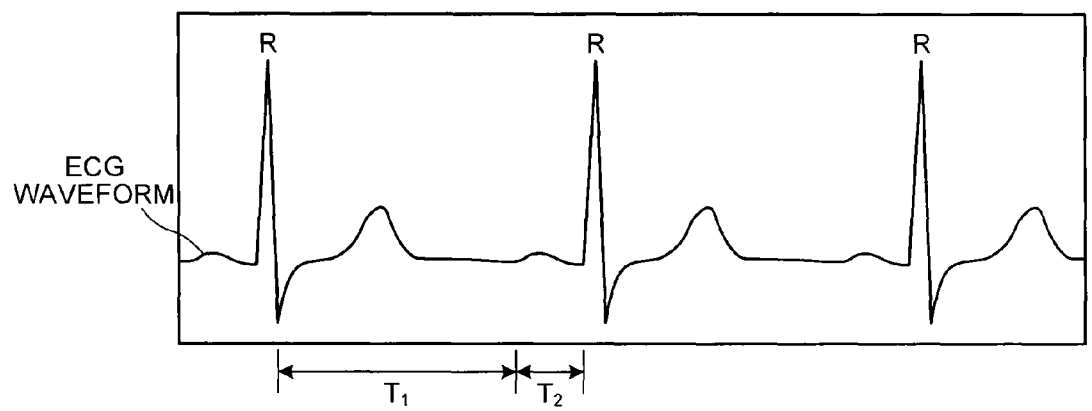
FIG. 8 is an explanatory diagram of an example of a process performed by an injector control unit according to a second embodiment.

A case where a contrast media concentration of a blood vessel region in an X-ray image is used as the blood flow state information has been explained in the first embodiment. However, the embodiment is not limited thereto and, for example, the ECG waveform can be used as the blood flow state information. FIG. 8 is an explanatory diagram of an example of a process performed by the injector control unit 212 according to a second embodiment.

In this case, the acquisition unit 211 according to the second embodiment acquires the ECG of the subject as the blood flow state information. The injector control unit 212 according to the second embodiment controls at least one of the injection start, the injection speed, and the injection amount of injection of the contrast media into the subject by the injector based on waveform information of the ECG acquired by the acquisition unit 211.

For example, the acquisition unit 211 acquires an ECG waveform collected from the subject P, as shown in FIG. 8. The injector control unit 212 decreases the injection amount of the contrast media during "$T_1$" between R waves of the ECG waveform, which is a section of a predetermined time from immediately after an R wave, as shown in FIG. 8. The injector control unit 212 increases the injection amount of the contrast media during "$T_2$", which is a section until another R wave after "$T_1$".

That is, the injector control unit 212 according to the second embodiment increases the amount of the contrast media at a timing when the amount of blood pumped from the heart becomes high and decreases the amount of the contrast media at a timing when the amount of blood pumped from the heart becomes low. Accordingly, the used amount of the contrast media can be suppressed appropriately without image processing.

While a case where the injector is controlled using the relative concentration has been explained in the first embodiment, the X-ray diagnostic apparatus 100 according to the present application can control the injector using an absolute value. That is, the X-ray diagnostic apparatus 100 according to the present application can control the injector based on whether a pixel value of each region exceeds or falls below a predetermined threshold (an absolute value).

The case where the start and the stop of injection of the contrast media is controlled using a predetermined threshold has been explained in the first embodiment as an example. However, the embodiment is not limited thereto and, for example, the injection speed can be changed according to the pixel value of each region without stopping injection of the contrast media. As an example, a control can be executed in such a manner that the injection speed of the contrast media is decreased when the pixel value of each region exceeds a predetermined threshold and the injection speed of the contrast media is increased when the pixel value of each region falls below the predetermined threshold.

The control of the injection speed of the contrast media is not only increasing or decreasing of the injection speed based on the threshold as mentioned above but also can be changing of the rate according to the pixel values. For example, the injection speed is associated with the pixel value to be inversely proportional to the pixel value, and a control is executed to gradually decrease the injection speed with increases of the pixel value and to gradually increase the injection speed when the pixel value starts decreasing. Accordingly, the pixel value in a region can be controlled to be substantially constant.

Figure 9:
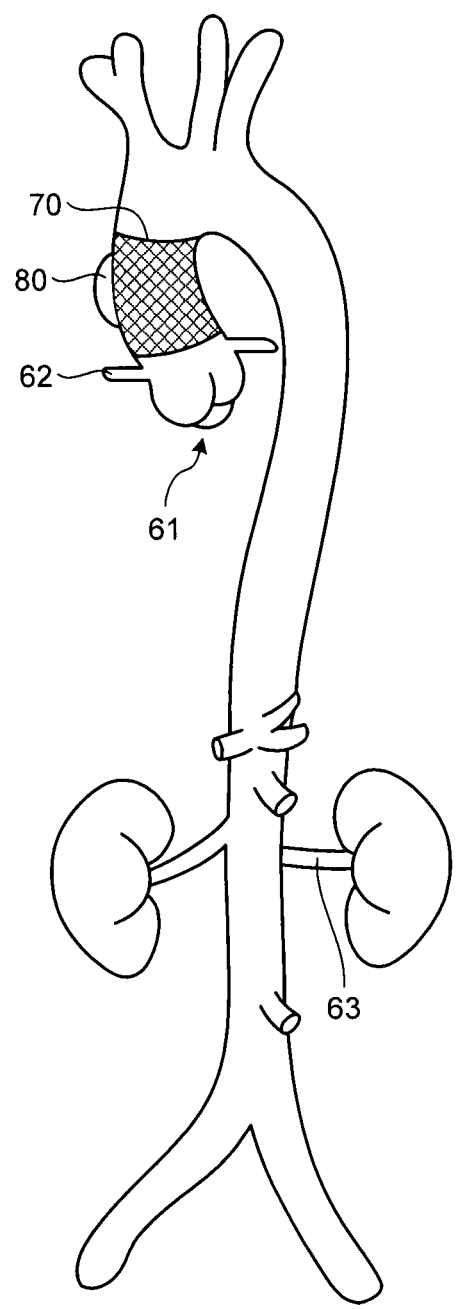
FIG. 9 is an explanatory diagram of a usage example of an X-ray diagnostic apparatus according to the second embodiment.

As mentioned above, the X-ray diagnostic apparatus 100 according to the present application can appropriately suppress the used amount of the contrast media by controlling the injection of the contrast media based on blood vessel state information such as the signal value (the concentration of the contrast media) in a blood vessel region within an X-ray image or the ECG waveform. A usage example of the X-ray diagnostic apparatus 100 according to the present application is explained with reference to FIG. 9. FIG. 9 is an explanatory diagram of a usage example of the X-ray diagnostic apparatus 100 according to the present embodiment. FIG. 9 shows an aorta through which blood is pumped from a heart.

For example, the X-ray diagnostic apparatus 100 according to the present application can appropriately suppress the used amount of the contrast media injected to observe the motion, the size, and the like of an aortic valve 61 shown in FIG. 9 in detail. As an example, when the aortic valve is to be observed, a catheter is inserted into the aorta and the contrast media is injected thereinto. However, in the case of a great artery such as the aorta, the contrast media flows together with blood pumped from the heart. If a conventional X-ray diagnostic apparatus is used in this case, the contrast media is injected under a fixed condition and thus the used amount reaches the limit at an early stage. On the other hand, when the X-ray diagnostic apparatus 100 according to the present application is used, the injection start, the injection stop, the injection speed, the injection amount, and the like of the contrast media can be controlled according to the concentrations of the contrast media near the aortic valve and thus the used amount of the contrast media can be suppressed appropriately. That is, the X-ray diagnostic apparatus 100 according to the present application appropriately allocates the limited used amount of the contrast media according to situations when a desired region is to be contrasted and observed, so that X-ray images that are easy to observe can be provided for a long time.

Accordingly, also in a case where an aortic valve replacement is performed after observing the motion, the size, and the like of the aortic valve 61 in detail, confirmation of the position of a prosthetic valve, confirmation of presence of an influence on coronary arteries 62, and the like can be performed more carefully. The X-ray diagnostic apparatus 100 according to the present application can reduce burdens on a subject by appropriately suppressing the used amount of the contrast media.

The usage example mentioned above is merely an example and the X-ray diagnostic apparatus 100 according to the present application can be used in other various situations. For example, when the stent-graft insertion technique to indwell a stent 70 is performed for an aortic aneurysm 80 shown in FIG. 9, X-ray images captured using the contrast media are observed to indwell the stent 70, to confirm invasion of blood into the aortic aneurysm 80 after indwelling of the stent 70, to confirm whether there is an influence on the coronary arteries 62 due to indwelling of the stent 70, and the like. When the X-ray diagnostic apparatus 100 according to the present application is used also in such a case, the X-ray images can be observed for a longer time than ever before and the confirmation can be performed more carefully.

The stent-graft insertion technique is performed not only at the position shown in FIG. 9 but may be also performed at any position in a thoracic aorta or an abdominal aorta. For example, the stent-graft insertion technique is performed at a position near various arteries that branch off from the aorta, such as a renal artery 63 that supplies blood to the kidneys or a superior mesenteric artery located above the renal artery 63 as shown in FIG. 9. Also at this time, confirmation of presence of an influence on each of the arteries due to indwelling of a stent can be performed more carefully by using the X-ray diagnostic apparatus 100 according to the present application.

As described above, the X-ray diagnostic apparatus 100 according to the present application can enhance accuracy of the procedures that use the contrast media and reduce burdens on a subject by appropriately suppressing the used amount of the contrast media. Furthermore, the X-ray diagnostic apparatus 100 according to the present application can not only execute a control to simply reduce the used amount of the contrast media but also improve the injection method of the contrast media according to situations of the moment. That is, the X-ray diagnostic apparatus 100 can arbitrarily control the injection start, the injection stop, the injection speed, the injection amount, and the like of the contrast media.

Because the X-ray diagnostic apparatus 100 can calculate how each of finely-divided regions in the same blood vessel is dyed by the contrast media, modification of the position of a catheter, suggestion of the type of a catheter to be used, and the like can be also performed by using calculated data. For example, by referring to data of how each of finely-divided regions in the same blood vessel is dyed, provided by the X-ray diagnostic apparatus 100, the position of a catheter can be modified to better dye a desired region in the blood vessel.

Another Embodiment

Figure 10:
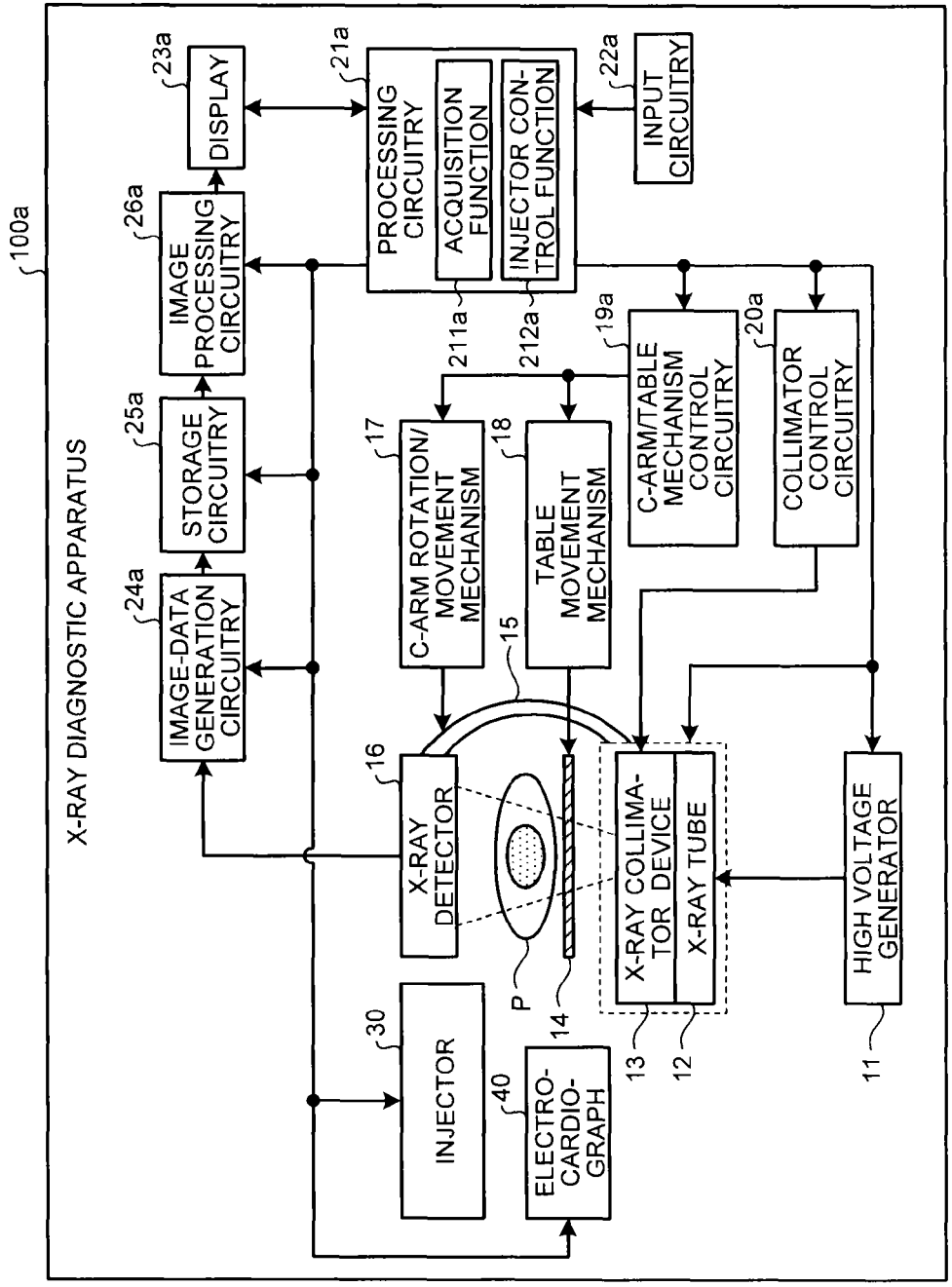
FIG. 10 is a diagram illustrating an example of the configuration of an X-ray diagnostic apparatus according to another embodiment.

Another embodiment of the X-ray diagnostic apparatus described above will be described with reference to FIG. 10. FIG. 10 is a diagram illustrating an example of the configuration of an X-ray diagnostic apparatus 100a according to another embodiment. In another embodiment, the points different from the above embodiments are mainly explained, and as for functions similar to the components explained in the above embodiment, the same reference numerals are given thereto, and explanation thereof is omitted. As illustrated in FIG. 10, the X-ray diagnostic apparatus 100a according to another embodiment includes the high voltage generator 11, the X-ray tube 12, the X-ray collimator device 13, the table 14, a C-arm 15, and an X-ray detector 16. The X-ray diagnostic apparatus 100a also includes the C-arm rotation/movement mechanism 17, the table movement mechanism 18, a C-arm/table mechanism control circuitry 19a, a collimator control circuitry 20a, a processing circuitry 21a, an input circuitry 22a, and a display 23a. The X-ray diagnostic apparatus 100a further includes an image-data generation circuitry 24a, a storage circuitry 25a, and an image processing circuitry 26a. The X-ray diagnostic apparatus 100a is connected to the injector 30 and the electrocardiograph 40. As illustrated in FIG. 10, each circuitry is connected in each other and to transmit and receive various signals to each other.

The C-arm/table mechanism control circuitry 19a corresponds to the C-arm/table mechanism control unit 19 illustrated in FIG. 1. The collimator control circuitry 20a corresponds to the collimator control unit 20 illustrated in FIG. 1. The processing circuitry 21a corresponds to the system control unit 21a illustrated in FIG. 1. The input circuitry 22a corresponds to the input unit 22 illustrated in FIG. 1. The display 23a corresponds to the display unit 23 illustrated in FIG. 1. The image-data generation circuitry 24a corresponds to the image-data generation unit 24 illustrated in FIG. 1. The storage circuitry 25a corresponds to the image-data storage unit 25 illustrated in FIG. 1. The image processing circuitry 26a corresponds to the image processing unit 26 illustrated in FIG. 1.

In the present embodiment, the respective processing functions performed by the C-arm/table mechanism control circuitry 19a, the collimator control circuitry 20a, the processing circuitry 21a, the image-data generation circuitry 24a, and the image processing circuitry 26a illustrated in FIG. 10 are stored in the storage circuitry 25a, in the form of a computer-executable program. Each of the C-arm/table mechanism control circuitry 19a, the collimator control circuitry 20a, the processing circuitry 21a, the image-data generation circuitry 24a, and the image processing circuitry 26a is a processor that loads programs from the storage circuitry 25a, and executes the programs so as to implement the respective functions corresponding to the programs. In other words, each circuitry that has loaded the programs has the functions corresponding to the programs loaded.

The term "processor" used in the above description means, for example, a central preprocess unit (CPU) and a graphics processing unit (GPU), or a circuit such as an application specific integrated circuit (ASIC), a programmable logic device (for example, a simple programmable logic device (SPLD)), a complex programmable logic device (CPLD), and a field programmable gate array (FPGA). The processor implements a function by loading and executing a program stored in a storage circuit. Instead of being stored in a storage circuit, the program may be built directly in a circuit of the processor. In this case, the processor implements a function by loading and executing the program built in the circuit. The processors in the present embodiment are not limited to a case in which each of the processors is configured as a single circuit. A plurality of separate circuits may be combined as one processor that implements the respective functions.

The storage circuitry 25a, for example, stores therein computer programs corresponding to an acquisition function 211a and an injector control function 212a illustrated in FIG. 10. The processing circuitry 21a reads the program corresponding to the acquisition function 211a from the storage circuitry 25a and executes the program, thereby performing processing similar to the acquisition unit 211. The processing circuitry 21a reads the program corresponding to the injector control function 212a from the storage circuitry 25a and executes the program, thereby performing processing similar to the injector control unit 212. The storage circuitry 25a, for example, also stores therein computer programs corresponding to a processing function to control the entire of the X-ray diagnostic apparatus 100a. The processing circuitry 21a reads the program corresponding to the processing function from the storage circuitry 25a and executes the program, thereby performing processing similar to the system control unit 21.

The storage circuitry 25a, for example, stores therein computer programs corresponding to a C-arm/table mechanism control function, a collimator control function, an image-data generation function, and an image processing function. Each of the C-arm/table mechanism control circuitry 19a, the collimator control circuitry 20a, the image-data generation circuitry 24a, and the image processing circuitry 26a reads the program corresponding to the C-arm/table mechanism control function, the collimator control function, the image-data generation function, and the image processing function from the storage circuitry 25a and executes the program respectively, thereby performing processing similar to the C-arm/table mechanism control unit 19, the collimator control unit 20, the image-data generation unit 24, and the image processing unit 26.

The example illustrated in FIG. 10 describes a case of implementing the acquisition function 211a and the injector control function 212a by causing one processing circuitry 21a to execute the respective programs. However, embodiments are not so limited, and for example, a plurality of processing circuits may implement the acquisition function 211a and the injector control function 212a. For example, one function among the acquisition function 211a and the injector control function 212a may be separately implemented in exclusive, independent program execution circuits.

Some of the circuitry illustrated in FIG. 10 may be implemented as one processing circuit. For example, one program execution circuit may implement the C-arm/table mechanism control function implemented by the C-arm/table mechanism control circuitry 19a, the collimator control function implemented by the collimator control circuitry 20a, the image-data generation function implemented by the image-data generation circuitry 24a, the image processing function implemented by the image processing circuitry 26a, and the processing function, the acquisition function 211a and the injector control function 212a implemented by the processing circuitry 21a.

The input circuitry 22a is implemented by a trackball, a switch button, a mouse, a keyboard, or the like for performing the setting of a ROI (region of interest) or the like. The input circuitry 22a is connected to the processing circuitry 21a, converts input operation received from an operator into an electric signal, and outputs the electric signal to the processing circuitry 21a.

Step S101 to step S104 in FIG. 7 is a step implemented by causing the processing circuitry 21a to read the program corresponding to the acquisition function 211a from the storage circuitry 25a and to execute the program. Step S105 to step S108 in FIG. 7 is a step implemented by causing the processing circuitry 21a to read the program corresponding to the injector control function 212a from the storage circuitry 25a and to execute the program. The above-described processing circuitry 21a is an example of a processing circuitry in the claims.

As explained above, the X-ray diagnostic apparatus and the injector according to the first and second embodiments can appropriately suppress the used amount of a contrast media.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. An X-ray diagnostic apparatus, comprising:
   processing circuitry configured to
      acquire pixel values of pixels included in a predetermined region in each of X-ray images that are collected chronologically as blood flow state information indicating a blood flow state in a blood vessel of a subject, and
      control at least one of an injection start, an injection speed, and an injection amount of injection of a contrast media into the subject by an injector according to changes of the pixel values, while acquiring the pixel values.
2. The X-ray diagnostic apparatus according to claim 1, wherein the processing circuitry is further configured to acquire the pixel values in each of a plurality of regions included in the X-ray images, and change a control related to the injection of the contrast media into the subject by the injector in accordance with changes of the acquired pixel values, according to respective importance of the regions.

3. The X-ray diagnostic apparatus according to claim 1, wherein the processing circuitry is further configured to acquire a difference between the pixel values of a first region included in the blood vessel region of the X-ray images and a second region included in a non-blood vessel region of the X-ray images, and execute a control according to changes of the difference between the pixel values acquired.

4. The X-ray diagnostic apparatus according to claim 1, wherein the processing circuitry is further configured to acquire a difference between the pixel values, which are acquired before and after contrasting of the blood vessel region of the X-ray images, and execute a control according to changes of the difference between the pixel values acquired.

5. The X-ray diagnostic apparatus according to claim 3, wherein the processing circuitry is further configured to extract the blood vessel region from the X-ray images, which are collected before and after contrasting using the contrast media.

6. The X-ray diagnostic apparatus according to claim 1, wherein the processing circuitry is further configured to control a contrast media injection condition including timings of the injection start and an injection stop of the contrast media by the injector, the injection speed of the contrast media, and the injection amount of the contrast media based on the blood flow state information acquired.

7. An injector that performs injection of a contrast media according to a control executed by the X-ray diagnostic apparatus according to claim 1.

8. An injector that performs injection of a contrast media according to a control executed by the X-ray diagnostic apparatus according to claim 2.

9. An injector that performs injection of a contrast media according to a control executed by the X-ray diagnostic apparatus according to claim 3.

10. An injector that performs injection of a contrast media according to a control executed by the X-ray diagnostic apparatus according to claim 4.

11. An injector that performs injection of a contrast media according to a control executed by the X-ray diagnostic apparatus according to claim 5.

12. An injector that performs injection of a contrast media according to a control executed by the X-ray diagnostic apparatus according to claim 6.

* * * * *